United States Patent
Ebner et al.

(10) Patent No.: US 8,903,350 B2
(45) Date of Patent: *Dec. 2, 2014

(54) METHOD FOR TRANSMITTING DATA IN A BLOOD GLUCOSE SYSTEM AND CORRESPONDING BLOOD GLUCOSE SYSTEM

(71) Applicant: LifeScan Scotland Limited, Inverness-shire (GB)

(72) Inventors: Manfred Ebner, Oberusel (DE); Ulrich Kraft, Hofheim (DE)

(73) Assignee: LifeScan Scotland Limited, Inverness (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,550

(22) Filed: Jun. 24, 2013

(65) Prior Publication Data

US 2013/0344813 A1    Dec. 26, 2013

Related U.S. Application Data

(63) Continuation of application No. 13/347,937, filed on Jan. 11, 2012, now Pat. No. 8,472,913, which is a (Continued)

(51) Int. Cl.
*H04B 7/00* (2006.01)
*A61M 5/172* (2006.01)
(Continued)

(52) U.S. Cl.
CPC ........ *A61M 5/1723* (2013.01); *H04W 52/0225* (2013.01); *A61B 5/0002* (2013.01); *A61B 5/14532* (2013.01); *A61B 5/4839* (2013.01); *A61B 2560/0209* (2013.01); *A61M 5/14244* (2013.01); *A61M 2205/3569* (2013.01); *A61M 2230/201* (2013.01); *H04W 52/0216* (2013.01); *H04B 7/24* (2013.01); *Y02B 60/50* (2013.01)
USPC .......... 455/343.3; 600/316; 600/345

(58) Field of Classification Search
CPC .................... H04W 52/0225; H04W 52/0229; H04W 52/0232
USPC ............................................ 455/343.3, 343.4
See application file for complete search history.

(56) References Cited

U.S. PATENT DOCUMENTS 5,394,882 A    3/1995 Mawhinney
5,566,081 A    10/1996 Yoshizawa et al.
(Continued)

FOREIGN PATENT DOCUMENTS

DE    10237692 A1    2/2004
EP    1473870 A2    11/2004
(Continued)

OTHER PUBLICATIONS

DDI, Diabetes Diagnostics Inc. "Galileo System RF Communication Protocol DS 1035837 Rev. 0.8," LifeScan, Inc. 2004, Schwalbach, Germany, 18 pages.

(Continued)

*Primary Examiner* — Thomas J Hiltunen

(57) ABSTRACT

The present invention relates to a method for wireless transmission of data between components of a blood glucose system (1, 11) including a master controller (2, 2') having a receiver (10) and a transmitter (9), and at least one slave device (3) having a receiver (19) and a transmitter (18). The slave device (3) is normally operated in a power saving mode and its receiver (19) is only activated intermittently at a receiver activation frequency for a predetermined listening period. The controller (2, 21) transmits a communication initiation data frame to the slave device (3) via a preamble signal transmitted for a preamble period. Upon receipt of the communication initiation data frame, the slave device (3) is switched to a communication mode in which it transmits a response to the controller (2, 21), and the slave device (3) is switched from the communication mode to the power saving mode.

17 Claims, 7 Drawing Sheets

Figure 1A:
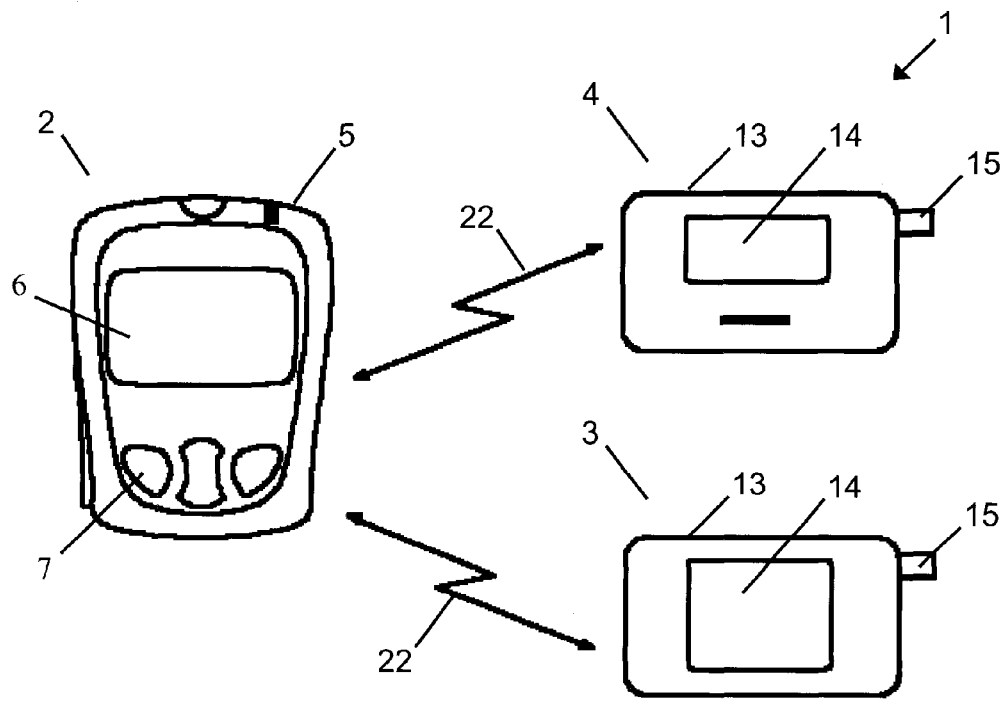

Related U.S. Application Data continuation of application No. 12/297,621, filed as application No. PCT/EP2006/003650 on Apr. 20, 2006, now Pat. No. 8,099,074.

(51) Int. Cl.
  *H04W 52/02* (2009.01)
  *A61B 5/00* (2006.01)
  *A61B 5/145* (2006.01)
  *H04B 7/24* (2006.01)
  *A61M 5/142* (2006.01)

(56) References Cited

U.S. PATENT DOCUMENTS

| | | | |
|---|---|---|---|
| 6,067,234 A | 5/2000 | Kim et al. | |
| 6,167,303 A | 12/2000 | Thompson | |
| 6,241,557 B1 | 6/2001 | Reichardt et al. | |
| 6,244,902 B1 | 6/2001 | McDowell et al. | |
| 6,579,498 B1 | 6/2003 | Eglise | |
| 6,585,644 B2 | 7/2003 | Lebel et al. | |
| 6,655,590 B1 | 12/2003 | McFeely et al. | |
| 6,731,962 B1 | 5/2004 | Katarow et al. | |
| 6,733,446 B2 | 5/2004 | Lebel et al. | |
| 6,807,159 B1 | 10/2004 | Shorey et al. | |
| 6,944,188 B2 * | 9/2005 | Sinha et al. | 370/503 |
| 7,356,041 B2 * | 4/2008 | Nielsen et al. | 370/431 |
| 7,546,090 B2 * | 6/2009 | Sayers | 455/78 |
| 8,064,594 B2 * | 11/2011 | Mohan et al. | 379/413.03 |
| 8,099,074 B2 * | 1/2012 | Ebner et al. | 455/343.3 |
| 8,295,196 B2 * | 10/2012 | Ergen et al. | 370/252 |
| 8,449,523 B2 * | 5/2013 | Brukalo et al. | 604/504 |
| 8,471,525 B2 * | 6/2013 | Kim et al. | 320/108 |
| 8,472,913 B2 * | 6/2013 | Ebner et al. | 455/343.3 |
| 2003/0065536 A1 | 4/2003 | Hansen et al. | |
| 2003/0087681 A1 | 5/2003 | Sackett et al. | |
| 2003/0114204 A1 | 6/2003 | Allen et al. | |
| 2003/0176183 A1 | 9/2003 | Drucker et al. | |
| 2003/0181798 A1 | 9/2003 | Al-Ali | |
| 2005/0163088 A1 | 7/2005 | Yamano et al. | |
| 2006/0248398 A1 | 11/2006 | Neel et al. | |
| 2008/0076969 A1 | 3/2008 | Kraft et al. | |
| 2009/0213830 A1 * | 8/2009 | Duesberg et al. | 370/345 |
| 2010/0303185 A1 * | 12/2010 | Haartsen | 375/362 |
| 2011/0176503 A1 * | 7/2011 | Patel et al. | 370/329 |

FOREIGN PATENT DOCUMENTS

| | | |
|---|---|---|
| JP | 2003520648 A | 7/2003 |
| JP | 2005217548 A1 | 8/2005 |
| JP | 2006140984 A | 6/2006 |
| JP | 09-065464 A | 3/2009 |
| WO | WO 02/37714 A1 | 5/2002 |
| WO | WO 03/096633 A1 | 11/2003 |
| WO | WO 2005/041432 A1 | 5/2005 |
| WO | WO 2006/026741 | 3/2006 |

OTHER PUBLICATIONS

Plexus "Galileo1 Final Design Presentation" LifeScan, Inc., Milpitas, California 43 pages.
International Search Report for PCT/EP2006/003650 dated Feb. 14, 2007, 6 pages.
Japanese Office Action, JP Application No. 2009-505725, dated Jan. 5, 2010, Patent Examining Division, Japan, 3 pages.
International Search Report for PCT/EP2006/004852 dated Jan. 30, 2007, 5 pages.
International Preliminary Examination Report for PCT/EP2006/011263 dated Jun. 4, 2009, 9 pages.

* cited by examiner

METHOD FOR TRANSMITTING DATA IN A BLOOD GLUCOSE SYSTEM AND CORRESPONDING BLOOD GLUCOSE SYSTEM

CROSS-REFERENCE

This application claims priority from prior filed U.S. patent application Ser. No. 13/347,937, filed Jan. 11, 2012, which claims priority to U.S. patent application Ser. No. 12/297, 621, filed Dec. 18, 2008 (now granted as U.S. Pat. No. 8,099, 074), which claims priority to International Application No. PCT/EP2006/003650, filed Apr. 20, 2006, all of the prior applications are hereby incorporated herein by reference as if fully set forth.

The present invention relates to a method for wireless transmission of data between components of a blood glucose system including a master controller and a slave device comprising an insulin dispensing means, and to a corresponding blood glucose system.

Diabetes mellitus is a chronic metabolic disorder caused by an inability of the pancreas to produce sufficient amounts of the hormone insulin so that the metabolism is unable to provide for the proper absorption of sugar and starch. This failure leads to hyperglycemia, i.e. the presence of an excessive amount of glucose within the blood plasma. Persistent hyperglycemia causes a variety of serious symptoms and life threatening long term complications such as dehydration, ketoacidosis, diabetic coma, cardiovascular diseases, chronic renal failure, retinal damage and nerve damages with the risk of amputation of extremities. Because healing is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External insulin was commonly administered by means of typically one or two injections of a mixture of rapid and intermediate acting insulin per day via a hypodermic syringe. While this treatment does not require the frequent estimation of blood glucose, it has been found that the degree of glycemic control achievable in this way is suboptimal because the delivery is unlike physiological insulin production, according to which insulin enters the bloodstream at a lower rate and over a more extended period of time. Improved glycemic control may be achieved by the so-called intensive insulinotherapy which is based on multiple daily injections, including one or two injections per day of long acting insulin for providing basal insulin and additional injections of rapidly acting insulin before each meal in an amount proportional to the size of the meal. Although traditional syringes have at least partly been replaced by insulin pens, the frequent injections are nevertheless very inconvenient for the patient.

Substantial improvements in diabetes therapy have been achieved by the development of blood glucose systems relieving the patient of the daily use of syringes or insulin pens. Such blood glucose systems usually comprise a battery-operated insulin pump and a separate battery-operated control unit. The insulin pump allows for the delivery of insulin in a more physiological manner and can be controlled to follow standard or individually modified protocols to give the patient a better glycemic control over the course of a day. It can be constructed as an implantable device for subcutaneous arrangement or can be constructed as an external device that is carried on the body of the patient.

The operation of the insulin pump can be controlled and modified by means of the control unit. For example, delivery of suitable amounts of insulin by the insulin pump requires that the patient frequently determines his or her blood glucose level and inputs this value into the control unit, which then calculates a suitable modification to the default or currently in use insulin delivery protocol, i.e. dosage and timing, and subsequently communicates with the insulin pump to adjust its operation accordingly. The determination of blood glucose concentration is performed by means of a suitable battery-operated measuring device such as a hand-held electronic meter which receive blood samples via enzyme-based test strips and calculates the blood glucose value based on the enzymatic reaction. Advantageously, the measuring device is an integral part of the blood glucose system, so that the measured value is automatically delivered to the control unit. In this regard, the measuring device may be integrated into the housing of the control unit or may be provided as a separate device communicating with the control unit. Further, it may be necessary to use the control unit each time the patient eats to instruct the pump to administer a specified amount of insulin to cover that meal. Recently, a more or less closed-loop control has been realized in which the control unit modifies the insulin delivery protocol automatically.

In view of the permanence of the therapy, it is desirable to provide the diabetic patient with flexibility, convenience and ease of use in order to increase the quality of his or her life. In this regard, it is evident that cable connections between the individual devices of a blood glucose system are disadvantageous. Thus, it is known to provide a wireless communication link. However, when implementing wireless communication, it has to be taken into account that the necessary receivers and transmitters are a main source of energy consumption. Thus, their use results in reduced battery life and necessitates a more frequent replacement or recharge of the batteries of the individual devices. In medical devices, this issue is not only inconvenient to the patient but also increases the danger of the devices not working properly when needed. Further, for implantable devices the replacement or recharge of the battery is accompanied by surgery. Therefore, it is important to provide for an efficient usage of the transmitters and receivers.

One possibility to reduce the energy consumption is the reduction of transmitting power. However, in many applications this is not sufficient. Therefore, the receivers and transmitters are commonly only activated regularly from time to time during distinct spaced listening and transmission periods, and synchronization means are provided which seek to maintain coincidence between the listening and transmission periods. With regard to battery life, it is desirable to reduce the duration of the individual listening and transmission periods and to increase the spacing between each two successive periods. Due to the spaced listening periods, it is, however, no longer possible to transmit a message immediately upon request. Rather, a device wishing to transmit a message to a particular recipient has to wait at least until the start of the next listening period of the recipient, and has further to wait for a confirmation of receipt at least until its own subsequent listening interval. Therefore, extended periods during which the receivers are deactivated have the disadvantage that they tend to result in substantial delay times which are inconvenient to the patient. Thus, there is a lower limit below which the spacing between successive listening periods should not fall if a suitable compromise between battery life and delay time is to be achieved.

One exemplary blood glucose system operating in this way is described in U.S. Pat. No. 6,585,644. This reference discloses a battery-operated external communication device that wirelessly communicates with at least one battery-operated medical device such as an implantable insulin pump and/or a blood glucose sensor via telemetry messages. The corresponding communication protocol is designed for low power consumption, in particular of the medical device(s), as well as for low communication delay times. According to the protocol, in all devices the receiver is activated only during distinct listening periods separated by periods of inactivity. The length of the listening periods determines the energy consumption, and the spacing between successive listening periods determines the delay time. The telemetry messages include a preamble portion which effects the transmission of a preamble signal upon transmission of the message. Transmission of telemetry messages occurs in corresponding transmission periods between which the transmitter is deactivated. The devices seek to stay synchronized with respect to each other such that the transmission and listening periods coincide. In case of failure of communication or loss of synchronization, the transmission periods may be extended or shifted, or the preamble signal may be transmitted over an extended period of time in order to catch a listening period of the target device. The implantable medical device may have a storage mode to which it can be shifted during periods of non-use and in which the spacing between successive listening periods is substantially increased to conserve battery power. This system has the disadvantages indicated above. It is still desirable to decrease the delay time further without substantially increasing energy consumption.

U.S. Pat. No. 6,807,159 discloses a protocol designed to reduce power consumption in master driven wireless networks without substantially increasing the delay time. The master regularly transmits a polling message to the slave devices which only activate their receiver during the transmission of this message. For each slave device, a probability based approach is used in order to predict the arrival time of the next data packet. The result of this prediction is then used to adjust the polling interval for each slave device. This adaptive probability based polling interval mechanism can lead to an optimization with respect to battery life and delay time if the time distribution of the traffic at each device is approximately constant. However, the mechanism cannot be applied advantageously to wireless blood glucose systems in which communication between the controller and the other devices of the system takes place only from time to time, so that the traffic distribution is highly non-uniform.

It is the object of the present invention to provide a method for wireless transmission of data between components of a blood glucose system that combines a low power consumption of all components of the system with low delay times and that remedies the disadvantages found in the prior art, and to provide a corresponding blood glucose system.

This object is achieved by a method with the features of claim 1 and by a blood glucose system with the features of claim 13. Further preferred embodiments of the invention are the subject-matter of the respective dependent claims.

The steps of the method of the present invention are performed by the components of a blood glucose system that includes an insulin dispensing device and a separate remote controller in order to wirelessly transfer commands, statuses and other data between the individual devices of the system. The data stream between the devices follows the master-slave-principle, wherein the remote controller is the master and the insulin dispensing device and possible further devices are slaves which in the usual manner never initiate a communication but only respond to messages received from the remote controller, i.e. only the master has the right to initiate a communication cycle, whereas the slave devices only transmit when requested by the master to ensure that two slave devices can never occupy the air interface at the same time. Each of the devices of the blood glucose system includes a receiver and a transmitter for wireless receipt and transmission, respectively, of messages.

The insulin dispensing device normally operates in a power saving mode in which its receiver is activated intermittently at a receiver activation frequency, with the receiver each time being activated for a predetermined listening period and the receiver being deactivated for the rest of the time. In a preferred embodiment, the predetermined listening period can e.g. be 10 ms. In case it is intended to use the controller to transmit data to the insulin dispensing device or to request a response from the insulin dispensing device, the transmitter of the controller is activated for a transmission period to transmit a suitable data frame addressed to or intended for the insulin dispensing device. Obviously, apart from the cases in which the blood glucose system does not include a further slave device in addition to the insulin dispensing device or in which it is intended to transmit the data frame to all slave devices of the blood glucose system, the data frame preferably includes an indication that the data frame is addressed to the insulin dispensing device. The data frame includes a preamble portion which is adapted such that upon transmission of the data frame a preamble signal is transmitted for a preamble period. All or some of the data frames may be communication initiation data frames. This type of data frame is transmitted by the controller if it wishes to establish communication with the insulin dispensing device. Following transmission of the communication initiation data frame, the transmitter of the controller is deactivated, and then the receiver of the controller is activated for a response period. In a preferred embodiment, the response period can e.g. be 50 ms to 500 ms and preferably about 100 ms. In any case, the chosen response period must sufficiently exceed the command processing times of the slave devices and must be sufficiently short to meet the desired performance and responsiveness requirements. In case the slave device receives the preamble signal, i.e. at least a part of the preamble included in the preamble portion of the communication initiation data frame, during a listening period, the receiver of the insulin dispensing device is maintained active until at least a portion of the remainder of the communication initiation data frame has been received by the insulin dispensing device. Following receipt of a communication initiation data frame addressed to or intended for the insulin dispensing device, the insulin dispensing device is switched into a communication mode in which its transmitter is activated to transmit a response to the controller. This response is likewise constituted by a data frame and, depending on the type of data frame transmitted by the controller, may be a mere confirmation of receipt or may include further data requested by the controller. The response transmitted by the insulin dispensing device following receipt of a communication initiation data frame indicates to the controller that the insulin dispensing device indeed received the communication initiation data frame and switched to communication mode. Subsequently or in a further step, the insulin dispensing device is switched back from the communication mode to the power saving mode.

According to the invention, upon switching back from communication mode to power saving mode the receiver activation frequency is initially set to a first frequency value. If no communication initiation data frame is received by the insulin dispensing device during a predetermined power saving timeout period, the receiver activation frequency is set to a second frequency value smaller than the first frequency value, thereby providing a "high frequency" power saving mode and a "low frequency" power saving mode. On the other hand, if a communication initiation data frame has been received, the insulin dispensing device is switched to communication mode as described above. Thus, every time the insulin dispensing device has received a communication initiation data frame and communicated with the controller, the spacing between successive listening periods is initially chosen such that a very low delay time but a slightly higher energy consumption than usual results. Only after some time without a further communication initiation data frame addressed to or intended for the insulin dispensing device from the controller, the spacing between successive listening periods is chosen such that the delay time is increased and the energy consumption is decreased to its usual power saving value. This two-step process is advantageous for a blood glucose system, because the patient usually only uses the controller a few times a day (and overall communication between the controller and the insulin dispensing device only occurs from time to time), and only during such times, a high delay time is experienced as inconvenient.

It has been realized that most uses of the controller involve a plurality of messages being sent from the controller to the insulin dispensing device within a small period of time, i.e. the communication behavior is highly non-uniform. According to the method of the present invention, the delay time is reduced at each possible beginning of such an interval of high traffic.

In the communication initiation data frames transmitted by the controller, the length of the preamble portion is chosen such that the preamble period exceeds the length of the cycle duration corresponding to the first frequency value. If no response is received during the response period, i.e. in case the insulin dispensing device has apparently not received the preamble signal in one of its listening periods, the length of the preamble portion is increased such that the preamble period exceeds the length of the cycle duration corresponding to the second frequency value, and the communication initiation data frame is retransmitted with this modified preamble portion. Thus, the controller initially transmits the communication initiation data frame such that it is only received if the insulin dispensing device is in the "high frequency" power saving mode or if one of its listening periods happens to overlap with the transmission time of the preamble signal. If the communication initiation data frame is received by the insulin dispensing device, energy is saved because the communication initiation data frame is transmitted with a short preamble period. Only if this communication attempt is not successful, the communication initiation data frame is transmitted such that it is definitely received at the insulin dispensing device operating in the "low frequency" power saving mode.

The method of the present invention provides the advantage that for the particular non-uniform traffic pattern of a blood glucose system, a low energy consumption at both the remote controller and the insulin dispensing device is combined with a low response time of the insulin dispensing device to requests transmitted by the controller.

The method of the present invention can be advantageously applied in case the blood glucose system includes, in addition to the insulin dispensing device, a blood glucose sensing device which is likewise configured as a slave device, and/or possibly one or more other additional slave devices. All slave devices of such a system, i.e. the insulin dispensing device, the blood glucose sensing device and possibly other slave devices, perform the same steps as described above for the insulin dispensing device. Accordingly, with respect to wireless communication, the slave devices show an identical behavior, i.e. follow the same communication protocol.

In the case of a blood glucose system comprising more than one slave device, the controller may transmit data to a particular slave device or request a response from a particular slave device as described above for the insulin dispensing device, i.e. by activating the transmitter of the controller for a transmission period to transmit a suitable data frame addressed to this slave device. It is then preferred to include an indication of the target slave device for which the communication initiation data frame is intended in the communication initiation data frame transmitted by the controller in order to establish communication with the slave device. Upon receipt of the preamble signal by a slave device during one of its listening periods, its receiver is maintained active until the target device indication included in the communication initiation data frame has been received. At this point, it can be determined whether the communication initiation data frame is addressed to this slave device. Only if the communication initiation data frame is indeed addressed to this slave device, its receiver is maintained active until the remainder of the communication initiation data frame has been received and the slave device is switched into communication mode as described above. Otherwise, the slave device is maintained in the power saving mode. However, the activation frequency for the slave device is changed to a third frequency value greater than the second frequency value, and only if no communication initiation data frame is received for a predetermined timeout period, which may e.g. be identical to the above predetermined power saving timeout period, the activation frequency is changed back to the second frequency value. Thus, whenever a communication initiation data frame is received, a slave device reduces the delay time even if the communication initiation data frame is addressed to another slave device. This behavior is advantageous because it has been found that during any period of high traffic the controller will most likely not only communicate with one slave device but with all slave devices in turn. Preferably, the third frequency value and the first frequency value are chosen to be identical.

In a preferred embodiment, the first frequency value is chosen such that the receiver of the insulin dispensing device is activated every 100 to 500 ms, preferably every 300 ms, and the second frequency value is chosen such that the receiver of the insulin dispensing device is activated every 0.5 to 30 s, preferably every 2 to 20 s and most preferably about every 3 s. In this regard, it is advantageous if the activation period corresponding to the second frequency value is an integral multiple of the activation period corresponding to the first frequency value. It is evident that the frequency values are always a compromise between suitable response times and sufficiently low energy consumption and have to be chosen to meet the particular requirements. On the one hand, higher frequency values increase the energy consumption of the slave devices, but reduce the energy consumption of the controller because shorter preamble periods may be utilized. On the other hand, lower frequency values reduce the energy consumption of the slave devices, but result in longer delay times and, due to longer preamble periods being necessary, in an increased energy consumption of the controller. Further, the short and the long preamble periods utilized by the controller are preferably chosen such that they exceed the time period of the "high frequency" power saving mode and the "low frequency" power saving mode, respectively, by about 25 ms. Thus, in the most preferred embodiment, the preamble periods are approximately 325 ms and approximately 3025 ms, respectively. Further, it is preferred that the predetermined power saving timeout period is 10 s to 60 s and preferably about 15 s. The optimum value of the predetermined power saving timeout period for a particular application should be chosen on the one hand based on an estimation of the average time period between different user actions on the controller that require wireless communication, and on the other hand on an estimation of the time after which the user may be considered not to seek to invoke another user interaction requiring wireless communication. The above values for the various parameters result in a good balance between low energy consumption and low response time of the blood glucose system.

In the case of more than one slave device, it may be advantageous in some instances if the above method is modified such that, upon switching of a slave device from communication mode to power saving mode, the receiver activation frequency is immediately set to the second frequency value without first setting it to the first frequency value. This modified method can be advantageous if in all probability the controller polls each slave device exactly once during each communication period. In such a case, an additional power saving can be achieved on the side of the slave devices.

The method may involve that all data frames transmitted by the controller are communication initiation data frames. However, it is preferred that following transmission of a communication initiation data frame the controller also sends further data frames. Thus, in a preferred version of the method of the present invention, following transmission of a communication initiation data frame, the transmitter of the controller is activated for at least one further transmission period to transmit at least one further data frame addressed to or intended for the same slave device and including a preamble portion which is chosen such that the preamble signal is transmitted for a preamble period, and following transmission of each of the least one further data frame the receiver of the controller is activated for a response period, which in a preferred embodiment can be e.g. 50 ms to 500 ms, preferably about 100 ms. In order to provide a possibility for the slave devices to distinguish communication initiation data frames from further data frames and possibly to distinguish between different types of further data frames, all data frames transmitted by the controller include a command portion in which a command is included that identifies the content of the data frame. For any communication initiation data frame, a communication initiation command is included in the respective command portion to identify this data frame as a communication initiation data frame.

In case a slave device receives the preamble signal during a listening period while it is in the power saving mode, the receiver of the slave device is maintained active at least until the command included in the command portion of the data frame has been received, and the slave device is maintained in the power saving mode in case the command is not the communication initiation command. On the other hand, in case a slave device receives the preamble signal while it is in the communication mode, the receiver of the slave device is maintained active at least until the command included in the command portion of the data frame has been received. If the command is not the communication initiation command and the slave device is the intended recipient of the data frame, the receiver of the slave device is maintained active until the remainder of the data frame has been received, and then the transmitter of the slave device is activated and deactivated to transmit a response to the controller. Thus, the slave devices only respond to further data frames if they are already in communication mode. It should be noted that each slave device transmits a response upon receipt of the communication initiation data frame instructing this slave device to switch to communication mode, i.e. the communication initiation data frame starting a communication cycle, as well as upon receipt of any further data frame addressed to this slave device and received by this slave device when it is still in communication mode. Therefore, in each communication cycle with a particular slave device, all data frames transmitted by the controller to this slave device entail a response data frame transmitted by the slave device to the controller. Depending on the type of data frame transmitted by the controller, the response data frame may be a mere confirmation of receipt or may include further data requested by the controller.

In a preferred embodiment, the communication mode at a particular slave device is terminated if no communication initiation data frame or further data frame addressed to this slave device is received for a predetermined communication timeout period, and the communication mode is arranged such that the receiver of the respective slave device is maintained active whenever its transmitter is not activated to transmit a response. Thus, starting with the receipt of the communication initiation data frame a particular slave device is maintained in communication mode at least for the predetermined communication timeout period. In communication mode, the delay time is substantially zero as the receiver of the slave device is active all the time, so that efficient communication involving a plurality of further data frames and corresponding responses is achieved. In this way, a number of data frames can be transmitted to the slave device with substantially zero delay time. It is further preferred that at the controller the time since transmitting the last data frame to a particular slave device is tracked and that it is determined at the controller, prior to transmitting a further data frame to the same slave device, based on a comparison between the measured time and the predetermined communication timeout period whether this slave device is expected to still be in communication mode. If it is determined that the slave device is expected to still be in communication mode, the controller initially transmits the data frame such that the preamble period spans a time period shorter than the cycle durations corresponding to the first frequency value and the second frequency value. In fact, the preamble period can be chosen to have a minimum duration, such as e.g. about 25 ms, because in communication mode the receiver of the slave device is always activated. In this way, additional energy saving is achieved on the side of the controller. In a preferred embodiment, the predetermined communication timeout period is 0.2 to 2.5 s and preferably approximately 2 s.

In the case of such an extended communication mode, it is further preferred to provide the option of including a delay time period indication into a response transmitted by a slave device to a particular first data frame to indicate that the actual response will be transmitted later. With other words, in case a slave device determines that it cannot transmit a response within the response period following transmission of the data frame, it can indicate to the controller that there will be a delay in the response. Then the transmitter and the receiver of both the slave device and the controller are deactivated for the indicated delay time period. Only after the end of the indicated delay time period, the transmitter of the controller and the receiver of the slave device are activated, so that the controller may transmit a second data frame requesting the delayed response from the slave device and the slave device can receive this request. Upon receipt of the request data frame, the transmitter of the slave device is activated to transmit the requested response to the controller. In this way, the response period can be chosen to be relatively small in order to save energy.

In the case of such an extended communication mode in which a communication cycle involves a communication initiation data frame followed by one or more additional data frames, it is advantageous if the data frames transmitted by the controller and by the slave device(s) include a frame number or frame reference uniquely identifying the data frame within a particular communication cycle. For example, the communication initiation data frame may include the frame number 1, and the data frame transmitted by the addressed slave device in response to the communication initiation data frame may likewise include the frame number 1. For each additional data frame transmitted by the controller and the corresponding response data frame the frame number is increased by 1, i.e. the first additional data frame and the response data frame have the frame number 2, the second additional data frame and the response data frame have the frame number 3 on so on. In another example, the communication initiation data frame includes the frame number 1, the data frame transmitted by the addressed slave device in response to the communication initiation data frame includes the frame number 2, the first additional data frame transmitted by the controller includes the frame number 3, and so on. In any case, by means of such frame numbers or frame references it can be guaranteed that all commands issued by the controller by means of transmitting corresponding data frames are executed exactly once by the addressed slave device in a predetermined order. The controller knows which frame number or frame reference a response data frame confirming execution of a command must have, so that the controller may reissue the command until execution of the command is confirmed. Further, the slave device knows which frame number or frame reference the additional data frame corresponding to the next command in a sequence of commands must have, so that it may issue a warning in case a command in the sequence is missing, and so that executing a particular command more than once is prevented.

In order to further increase the safety of the blood glucose system, it is also advantageous if each data frame not only includes an indication of the addressed slave device (in case of more than one slave device), but also a source device reference uniquely identifying the device (controller or slave device) that transmitted the data frame. This source device reference may be utilized to ensure that the components of a particular blood glucose system disregard data frames not belonging to this blood glucose system.

In a further preferred embodiment, the controller may transmit a data frame including a termination command to a slave device in communication mode, and the slave device terminates the communication mode upon receipt of this termination data frame. Thus, in case it is not intended to use the controller to transmit a further data frame to a slave device in communication mode, the communication mode involving a substantially permanently activated receiver may be terminated prior to the end of the communication timeout period in order to save energy. This possibility of terminating the communication mode of a slave device is preferably combined with the above described embodiment in which the communication mode at a particular slave device is terminated if no communication initiation data frame or further data frame addressed to this slave device is received for a predetermined communication timeout period. It is then preferred that the communication mode should always be terminated by means of a termination command, and that the communication timeout period is only provided as a safety feature to avoid that in case of errors a slave device inadvertently remains in communication mode permanently.

It is further preferred that the transmission of at least one communication initiation data frame by the controller is initiated by user request, i.e. the communication initiation data frame is transmitted without waiting for some predetermined transmission window. This may be the case if the patient decides to modify the insulin delivery protocol or to change some other setting of a slave device, or if the patient needs to dispense insulin prior to a meal.

Additionally or alternatively, it is preferred that a timer event is periodically generated in the controller and that a communication initiation data frame is transmitted by the controller upon each occurrence of such a timer event. In this regard, it is particularly advantageous to choose the frequency at which the timer events occur to have the second frequency value or such that the second frequency value is an integral multiple of the timer event frequency, to include a time reference in each communication initiation data frame initiated by a timer event, to examine the time reference upon receipt at a slave device, and to synchronize, based on the time reference, the start times of the listening periods of the slave devices with the timer events. In this way, irrespective of the current activation frequency value of a target slave device, it is ensured that the controller can reach the target slave device using a preamble period that only needs to exceed the length of the cycle duration corresponding to the first frequency value. Thus, energy consumption as well as delay time are reduced. The timer event triggered transmission of a communication initiation data frame or autopolling is utilized e.g. for automatic control and maintenance of the slave devices. Thus, timer event generated communication cycles may serve to periodically check the status of the slave devices or to control the operation of the slave devices, e.g. to regularly dispense suitable amounts of insulin by means of the insulin dispensing device. Preferably, such timer events are generated every 3 to 5 min, preferably about every 5 min. Further, it may be advantageous if the communication initiation data frames transmitted upon occurrence of a timer event are distinguished from communication initiation data frames initiated by user request, and if the slave device receiving a communication initiation data frame determines whether the communication initiation data frame was initiated by a timer event or by user request. In this way, the communication timeout period, the power saving timeout period and/or the timeout period utilized by slave devices not addressed by a communication initiation data frame to determine when to change from "high frequency" power saving mode to "low frequency" power saving mode may be chosen to be shorter for a communication initiation data frame initiated by a timer event than for a communication initiation data frame initiated by user request. This can be advantageous, because in most instances autopolling does not require extended communication and because autopolling does not require user interaction so that extended delay times do not lead to user annoyance.

The present invention further relates to a blood glucose system implementing the method of the present invention. Such a system comprises a master controller having a receiver, a transmitter and a control means, wherein the control means is operable to activate the transmitter for a transmission period in order to transmit a communication initiation data frame including a preamble portion such that a preamble signal is transmitted for a preamble period, and to subsequently activate the receiver for a response period. The system further includes a slave device comprising an insulin dispensing means and having a receiver, a transmitter and a control means, wherein the slave device is adapted to be worn on or to be implanted subcutaneously into the body of a patient such that insulin can be delivered from the slave device to the body of the patient. The control means of the slave device is adapted to operate the slave device normally in a power saving mode in which the control means activates the receiver intermittently at a receiver activation frequency, with the receiver each time being activated for a predetermined listening period of e.g. 10 ms and the receiver being deactivated for the rest of the time. The control means of the slave device is further adapted to determine whether the receiver of the slave device receives the preamble signal of the communication initiation data frame during a listening period, and in case the preamble signal is received to maintain the receiver of the slave device active until at least a portion of the remainder of the communication initiation data frame has been received, switch the slave device to a communication mode in which the control means activates the transmitter of the slave device to transmit a response to the controller, and subsequently switch the slave device from the communication mode to the power saving mode. The response transmitted by the insulin dispensing device following receipt of a communication initiation data frame indicates to the controller that the insulin dispensing device indeed received the communication initiation data frame and switched to communication mode.

According to the present invention the control means of the slave device is adapted to initially set the activation frequency to a first frequency value upon switching the slave device from communication mode to power saving mode, and to set the activation frequency to a second frequency value smaller than the first frequency value if the receiver does not receive a communication initiation data frame intended for the slave device for a predetermined power saving timeout period, wherein the control means of the controller is adapted to transmit the communication initiation data frame such that the preamble period exceeds the length of the cycle duration corresponding to the first frequency value, and, in case no response is received during the response period, to adapt and retransmit the communication initiation data frame such that the preamble period is increased and exceeds the length of the cycle duration corresponding to the second frequency value.

In a preferred embodiment, the first frequency value is chosen such that the receiver of the slave device is activated every 100 to 500 ms, preferably every 300 ms, and the second frequency value is chosen such that the receiver of the slave device is activated every 0.5 to 30 s, preferably every 2 to 20 and most preferably about every 3 s. Further, the short and the long preamble periods utilized by the controller are preferably chosen such that they exceed the time period of the "high frequency" power saving mode and the "low frequency" power saving mode, respectively, by about 25 ms. Thus, in the most preferred embodiment, the preamble periods are approximately 325 ms and approximately 3025 ms, respectively. Further, it is preferred that the predetermined power saving timeout period is 10 s to 60 s and preferably about 15 s. These values result in a good balance between low energy consumption and low response time of the blood glucose system.

In a preferred embodiment, the system includes at least one further slave device, at least one of which comprises a blood glucose sensing means, wherein all slave devices comprise a receiver, a transmitter and a control means configured in the same way as the receiver, the transmitter and the control means, respectively, of the slave device comprising an insulin dispensing means. The control means of the controller is further adapted to include an indication of a target slave device in each communication initiation data frame in order to individually address the various slave devices. The control means of the slave devices is further adapted to maintain the receiver of the slave device active at least until the receiver has received the target device indication, and maintain the receiver of the slave device active until the remainder of the communication initiation data frame has been received and switch the slave device into communication mode if the slave device is the target slave device, or, in case the slave device is not the target device, maintain the slave device in the power saving mode, and set the receiver activation frequency for the slave device to a third frequency value, which is greater than the second frequency value and is preferably identical to the first frequency value and subsequently set the receiver activation frequency to the second frequency value if the receiver does not receive a communication initiation data frame for a predetermined timeout period, in case the control means determines that the slave device receives the preamble signal during a listening period.

It is further preferred that following transmission of a communication initiation data frame, the control means of the master controller is further operable to activate the transmitter of the controller for at least one further transmission period to transmit at least one further data frame addressed to or intended for the same slave device and including a preamble portion such that the preamble signal is transmitted for a preamble period, and following transmission of each of the least one further data frame to activate the receiver of the controller for a response period, which can e.g. be 50 ms to 500 ms and preferably about 100 ms, wherein all data frames transmitted by the controller include a command portion in which a command is included. The control means of the controller is further adapted to include a communication initiation command in the command portion of any communication initiation data frame to indicate that this data frame is a communication initiation data frame. The control means of the slave devices is further adapted to determine whether the receiver of the slave device receives the preamble signal during a listening period while it is in the power saving mode, and in case this determination is positive to maintain the receiver of the slave device active until the command included in the command portion of the data frame has been received, and maintain the slave device in the power saving mode in case the command is not the communication initiation command. The control means of the slave devices is further adapted to determine whether the receiver of the slave device receives the preamble signal while it is in the communication mode, and in case this determination is positive to maintain the receiver of the slave device active at least until the command included in the command portion of the data frame has been received, and if the command is not the communication initiation command and the slave device is the intended recipient of the data frame, maintain the receiver of the slave device active until the remainder of the data frame has been received, and activate and deactivate the transmitter of the slave device to transmit a response to the controller. It should be noted that each slave device transmits a response upon receipt of the communication initiation data frame instructing this slave device to switch to communication mode, i.e. the communication initiation data frame starting a communication cycle, as well as upon receipt of any further data frame addressed to this slave device and received by this slave device when it is still in communication mode. Therefore, in each communication cycle with a particular slave device, all data frames transmitted by the controller to this slave device entail a response data frame transmitted by the slave device to the controller. Depending on the type of data frame transmitted by the controller, the response data frame may be a mere confirmation of receipt or may include further data requested by the controller.

In a further preferred embodiment, the control means of each slave device is adapted to terminate the communication mode if the receiver does not receive a data frame for the respective slave device for a predetermined communication timeout period, and to maintain the receiver of the respective slave device active in communication mode whenever it does not activate the transmitter to transmit a response. In a preferred embodiment, the predetermined communication timeout period is 0.2 to 2.5 s and preferably approximately 2 s.

It is also preferred that the controller further includes a timer, and that the control means of the controller is adapted to start the timer upon transmitting a data frame to a particular slave device, to determine, prior to transmitting a data frame to the same slave device, based on a comparison between the current value of the timer and the predetermined communication timeout period whether the slave device is expected to still be in communication mode, and in case it determines that the slave device is expected to still be in communication mode to initially transmit the data frame such that the preamble period spans a time period shorter than the cycle durations corresponding to the first frequency value and the second frequency value.

It is further preferred that the control means of each slave device is adapted to include a delay time period indication into a response transmitted by the slave device to a particular first data frame to indicate that the actual response will be transmitted later, to deactivate the transmitter and the receiver for the indicated delay time period, to activate the receiver of the slave device after the end of the delay time period to wait for the receipt of a second data frame requesting the response to the first data frame, and to subsequently activate the transmitter of the slave device to transmit the requested response to the controller, and that the control means of the controller is adapted to deactivate, upon receipt of a response including a delay time period indication, the transmitter and the receiver of the controller for the indicated delay time period, and to activate the transmitter of the controller after the end of the delay time period to transmit a second data frame requesting the response to the first data frame.

In a preferred embodiment, the control means of the controller is operable to transmit a data frame including a termination command to a slave device in communication mode, and the control means of each slave device is adapted to terminate the communication mode upon receipt of this data frame. This possibility of terminating the communication mode of a slave device is preferably combined with the above described embodiment in which the communication mode at a particular slave device is terminated if no communication initiation data frame or further data frame addressed to this slave device is received for a predetermined communication timeout period. It is then preferred that the communication mode should always be terminated by means of a termination command, and that the communication timeout period is only provided as a safety feature to avoid that in case of errors a slave device inadvertently remains in communication mode permanently.

In a preferred embodiment, the controller comprises an actuation means, actuation of which provides a signal to the control means instructing the control means to transmit a data frame.

It is also preferred that the controller further comprises a timer event generator operable to periodically generate a timer event and to provide corresponding timer event signals to the control means of the controller, and that the control means of the controller is adapted to transmit a communication initiation data frame upon receipt of such a timer event signal. In this case, it is further preferred that the frequency with which the timer event generator generates the timer events has the second frequency value or is such that the second frequency value is an integral multiple of the timer event frequency, the controller comprises a clock and the control means of the controller is adapted to include a time reference derived from the clock in each data frame initiated by the receipt of a timer event signal, and the control means of the slave devices are adapted to examine the time reference upon receipt at a slave device, and to synchronize by means of the time reference the start times of the listening periods with the timer events. Preferably, the timer event generator is able to generate such timer events every 3 to 5 min, preferably about every 5 min.

In a preferred embodiment, the controller includes a blood glucose sensing means. Thus, the system may include a separate blood glucose sensing device configured as slave and/or may include a controller into which a blood glucose sensing device is integrated.

In the following, the invention is explained in more detail for a preferred embodiment with reference to the figures.

FIG. 1*a* shows a schematic representation of a blood glucose system according to the present invention.

Figure 1B:
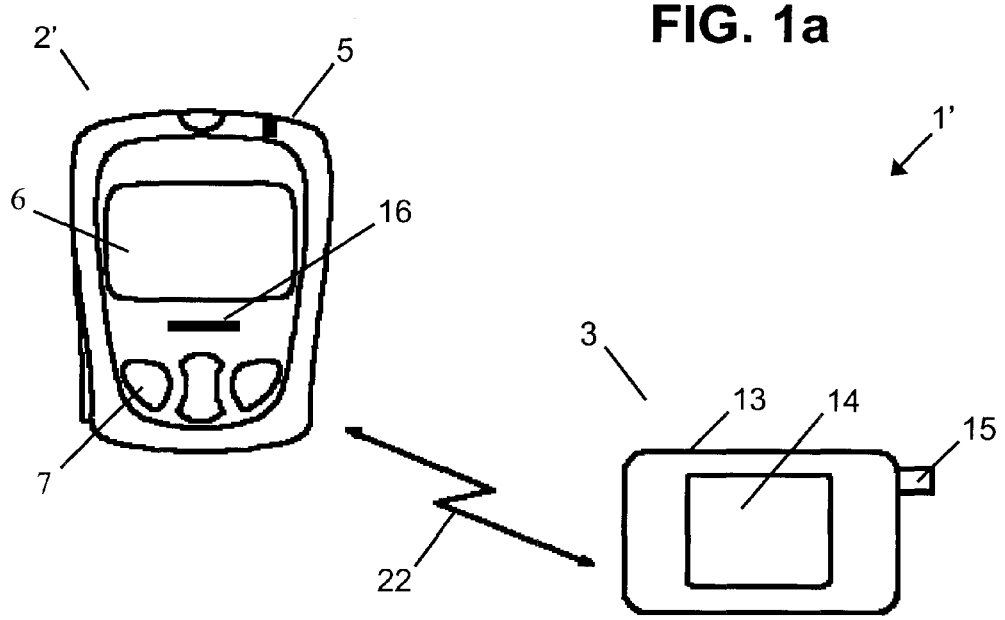

FIG. 1*b* shows a schematic representation of a further blood glucose system according to the present invention.

Figure 2A:
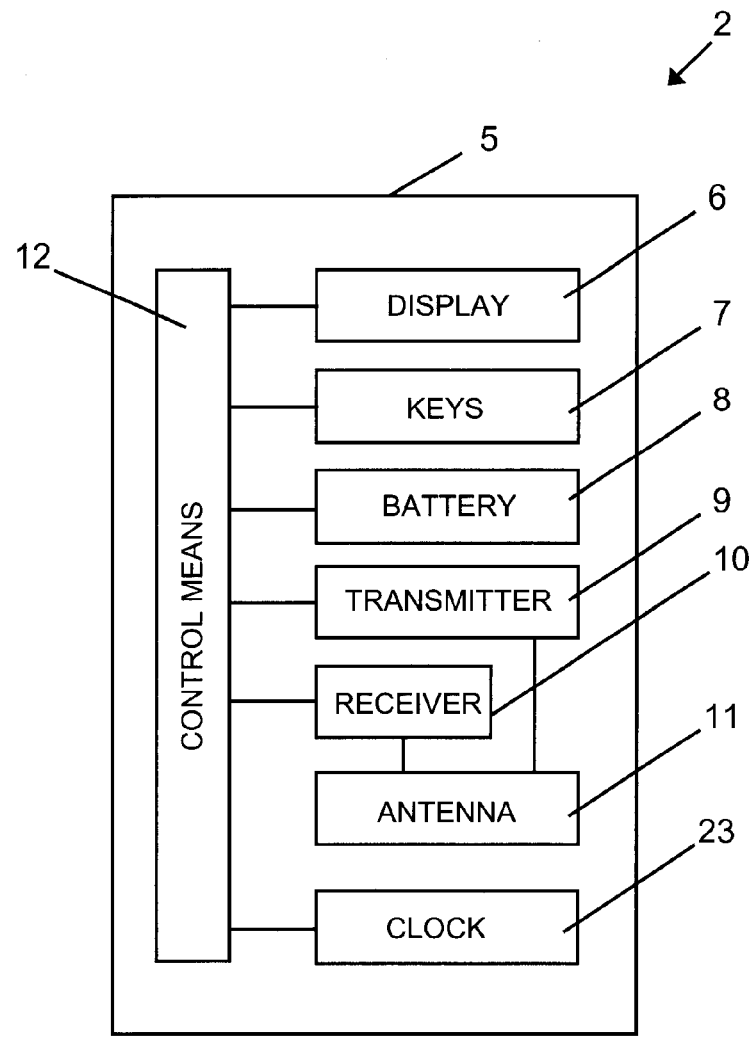

FIG. 2*a* shows a schematic block diagram of the main components of the controller forming part of a blood glucose system according to the present invention.

Figure 2B:
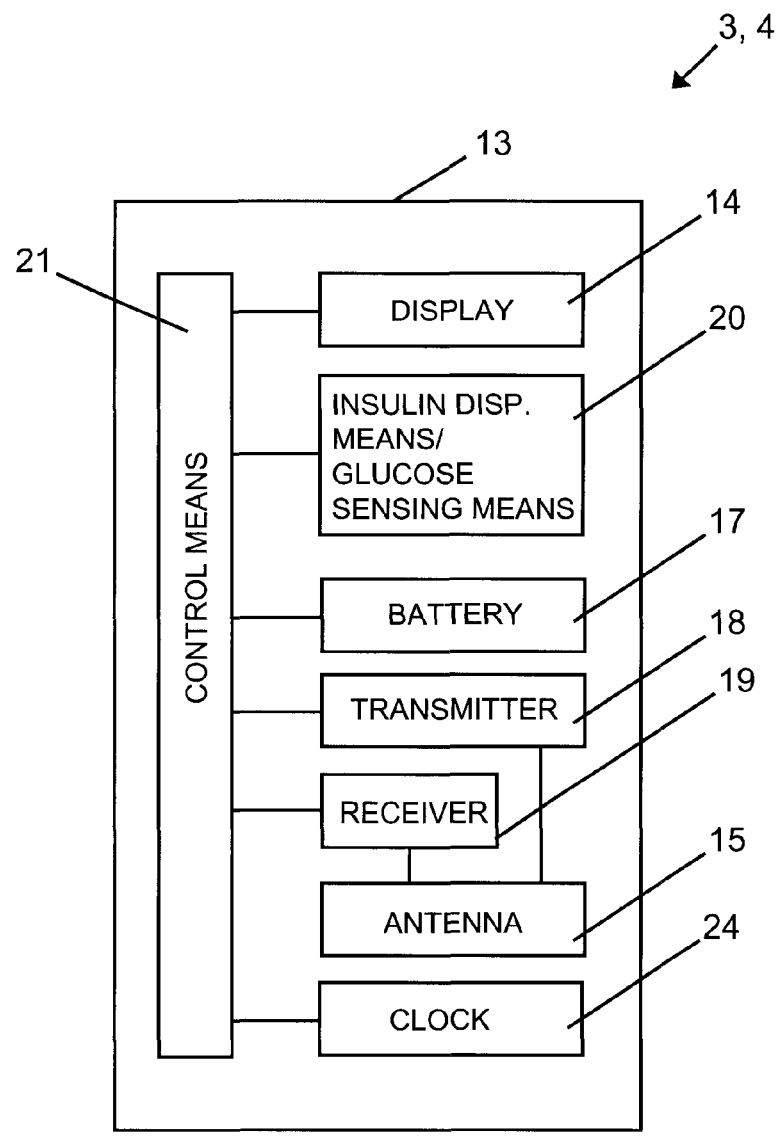

FIG. 2*b* shows a schematic block diagram of the main components of a slave device forming part of a blood glucose system according to the present invention.

Figure 3A:
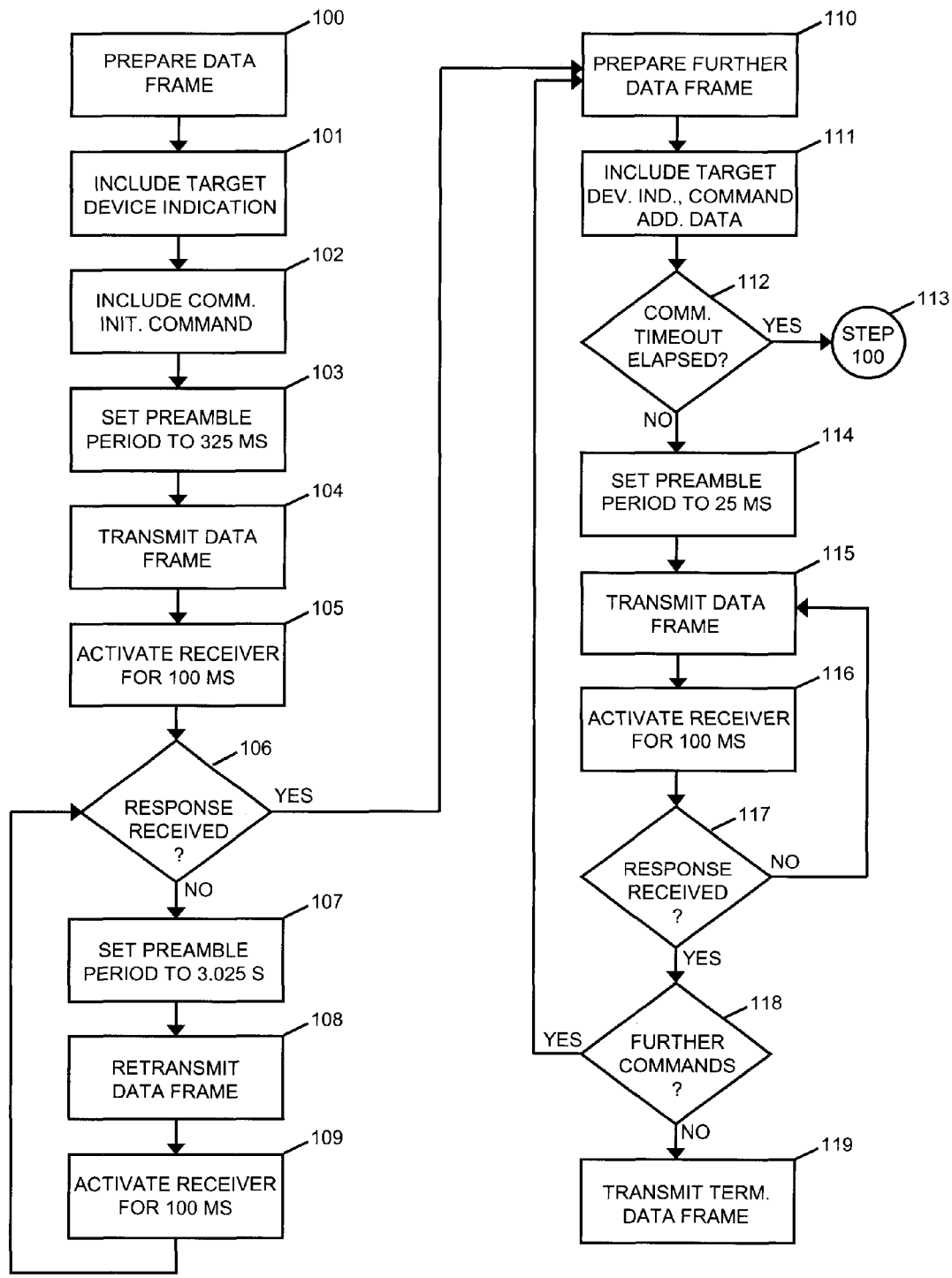

FIG. 3*a* is a schematic flowchart diagram illustrating the controller side of a preferred embodiment of the method in accordance with the present invention.

Figure 3B:
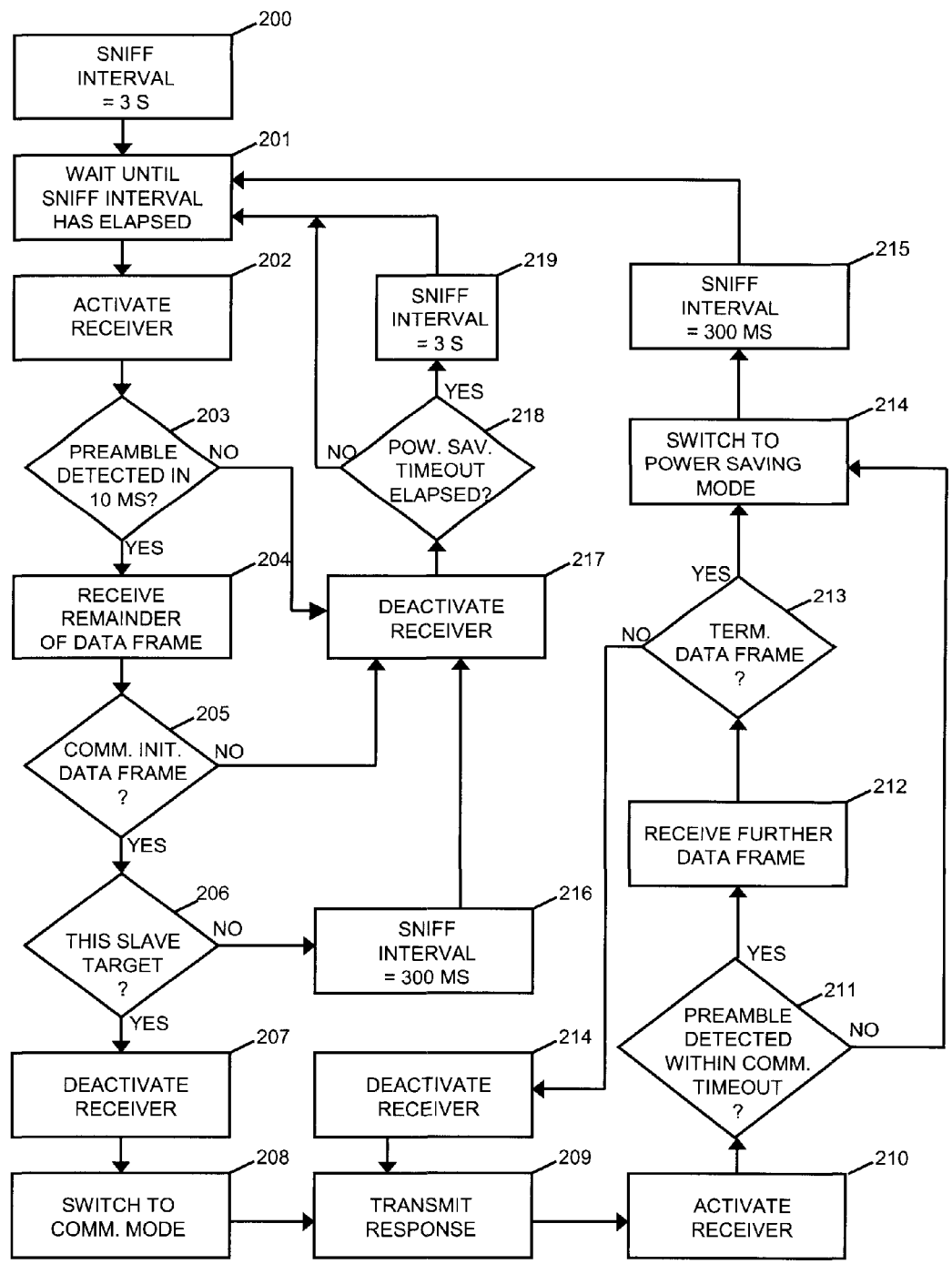

FIG. 3*b* is a schematic flowchart diagram illustrating the slave side of a preferred embodiment of the method in accordance with the present invention.

Figure 4:
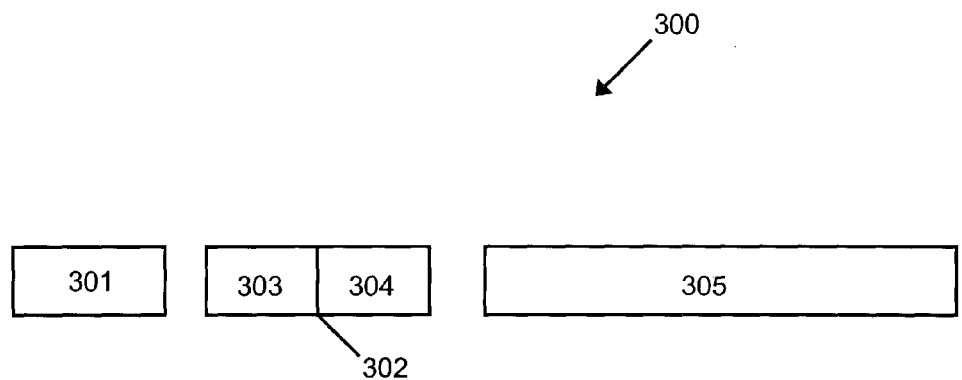

FIG. 4 is a schematic illustration of a data frame.

Figure 5A:
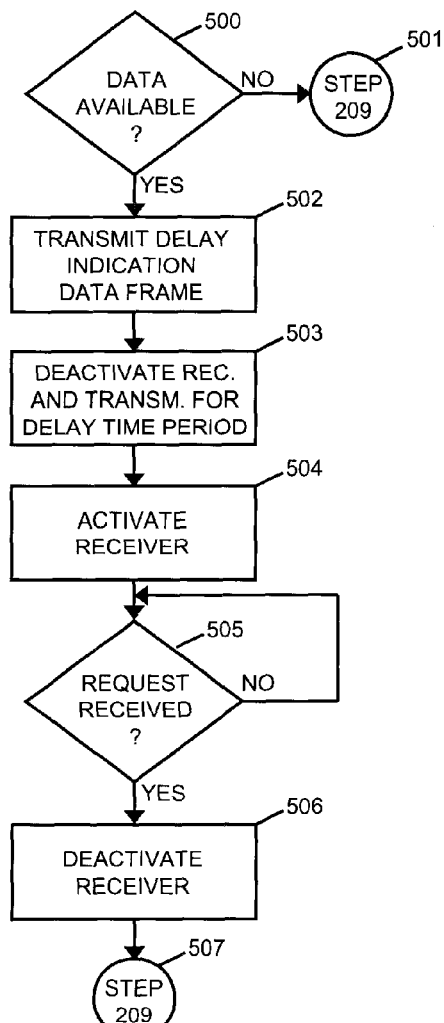

FIG. 5*a* is a schematic flowchart diagram illustrating the slave side of a delayed response mechanism.

Figure 5B:
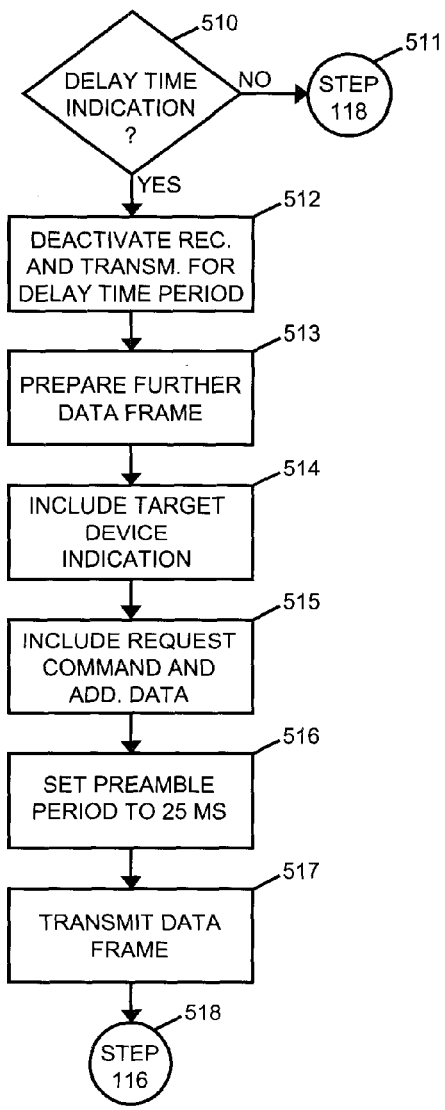

FIG. 5*b* is a schematic flowchart diagram illustrating the controller side of the delayed response mechanism.

In FIG. 1*a*, a blood glucose system 1 is schematically shown comprising a controller 2, an insulin pump 3 for dispensing insulin to the blood circuit of a patient, and a blood glucose measuring device 4 for determining the level of blood glucose. The controller 2 includes a housing 5, a display 6 and a number of control keys 7 which may be utilized to initiate a particular action by the controller 2 or to input data into the controller 2, e.g. in order to adjust the operation of the insulin pump 3 with regard to various patient parameters such as e.g. his or her weight. Further main components of the controller 2 are depicted in the schematic block diagram shown in FIG. 2*a*. Accordingly, the controller 2 further comprises a battery 8, a transmitter 9, a receiver 10, an antenna 11 coupled to the transmitter 9 and the receiver 10, and a clock 23. The operation of the controller 2 is controlled by control electronics 12. In particular, the control electronics 12 are operable to compose data frames to be transmitted by means of the transmitter 9, to analyze data frames received by the receiver 10, and to activate and deactivate the transmitter 9 and the receiver 10 to transmit and receive, respectively, data frames. By means of the clock 23, the control electronics 12 may provide timer functions (creating, starting and stopping timers) and to define and create timer events.

The insulin pump 3 and the blood glucose measuring device 4 each comprise a housing 13, a display 14 and an antenna 15. Further main components of the of the insulin pump 3 and the measuring device 4 are depicted in the schematic block diagram shown in FIG. 2b. Accordingly, the insulin pump 3 and the measuring device 4 further comprise a battery 17, a transmitter 18 and a receiver 19 which are both coupled to the antenna 15, and a clock 24. The operation of the controller 2 is controlled by control electronics 21. In particular, the control electronics 21 are operable to compose data frames to be transmitted by means of the transmitter 18, to analyze data frames received by the receiver 19, and to activate and deactivate the transmitter 18 and the receiver 19 to transmit and receive, respectively, data frames. By means of the clock 24, the control electronics 12 may provide timer functions (creating, starting and stopping timers) and to define and create timer events. Both devices also comprise a functional block 20. In the case of the insulin pump 3, the block 20 is an insulin dispensing means, whereas in the case of the blood glucose measuring device 4 the block 20 is a glucose sensing means that is able to analyze blood samples on enzyme-based test strips, that can be inserted into a test strip receiving slot 16, in order to determine the blood glucose level based on the enzymatic reaction. The controller 2 communicates with the devices 3 and 4 via an RF air interface 22, which may e.g. use a frequency of 869.84 MHz for Europe or 903.02 MHz for the US and Canada, a binary separation of 64 kHz and FSK modulation. Manchester coding may be utilized to allow for automatic balancing of the receivers and to test for Manchester violations. The data rate may e.g. be 9600 bps.

FIG. 1b schematically shows an alternative blood glucose system V. Like the system 1 of FIG. 1a, the system 1' comprises a controller 2' and an insulin pump 3 for dispensing insulin to the blood circuit of a patient. However, the system 1' does not comprise a separate blood glucose measuring device 4. Rather, a blood glucose measuring means and a test strip receiving slot 16' are integrated into the controller 2', i.e. the controller 2 and the blood glucose measuring device 4 of the system 1 shown in FIG. 1a are combined into a single device 2' having a common housing 5.

In FIGS. 1a and 1b, the insulin pump 3 is illustrated as an external device to be worn on the body of a patient. However, the insulin pump 3 may also be constructed as an implantable device to be disposed subcutaneously.

In the RF wireless network established by the controller 2, 2' and the devices 3 and 4, the controller 2, 2' is configured as master and the devices 3 and 4 are configured as slaves, i.e. they never initiate a communication but only respond to commands received from the controller 2, 2'. The controller 2, 2' and the slave devices 3, 4 communicate by exchanging data frames, wherein each transmission preferably consists of one data frame only. One such data frame 300 is shown schematically in FIG. 4. The data frame 300 comprises a preamble portion 301, an address header 302 (comprising a target address portion 303, a command portion 304 and optional further header portions (not shown) such as a checksum portion, a source address portion and/or a frame number or frame reference portion) and an optional data portion 305. The length of the preamble portion 301 is variable to includes an adjustable number of preamble bytes having a characteristic bit pattern (e.g. 01010101), so that upon transmission of the data frame a characteristic preamble signal is transmitted for an adjustable period of time (preamble period). Each data frame 300 is addressed to a particular recipient. In order to indicate the intended recipient, the sender includes a predefined target device address into the target address portion 303. The type of data frame, i.e. command or response, and the type of command are identified by a unique command or response identifier included in the command portion 304. Thus, upon receipt of a data frame 300, the control electronics 12, 21 can determine whether the respective device is the intended recipient. Further, it can be determined which command or response the controller 2, 2' or the devices 3, 4, respectively, have sent. Some commands may require further information to be transmitted to the recipient. Such information may be included into the optional data portion 305. The same applies to additional information, such as status data, transmitted as a response by the devices 3, 4.

In FIGS. 3a and 3b, schematic diagrams of a preferred embodiment of the method according to the present invention is shown, wherein FIG. 3a shows the steps performed in the controller 2, 2' and FIG. 3b shows the steps performed in the insulin pump 3 and the blood glucose measuring device 4.

According to the embodiment shown in FIG. 3b, the slave devices 3, 4 normally operate in a power saving mode in which their transmitter 18 and receiver 19 are usually deactivated and in which the receiver 19 is only activated every 3 s for a listening period of 10 ms. Such a mode of operation is commonly termed sniff mode, and the interval between the start times of successive listening periods is referred to as the sniff interval. Thus, the operation of the slave devices 3, 4 starts in step 200, in which the sniff interval is set to 3 s. After the sniff interval has elapsed (step 201), the receiver 19 is activated in step 202, and in step 203 it is determined whether a preamble signal can be detected during the listening period of 10 ms. If this is the case, the receiver 19 is maintained active to receive the remainder of the data frame (step 204). Subsequently, the command portion 304 of the received data frame 300 is examined to determine whether it includes the communication initiation command identifier. This particular command is used by the controller 2, 2' to switch the target device into a communication mode in which the receiver 19 is activated essentially all the time. Accordingly, if it is determined in step 206 that the target address portion 303 includes the address of the respective slave device, the receiver is deactivated (step 207) and the slave device is switched to communication mode (step 208).

In communication mode, the transmitter 18 is activated and deactivated to transmit a response to the controller 2, 2' (step 209), and then the receiver 19 is again activated (step 210) to wait for further data frames 300 from the controller 2, 2'. The response to the communication initiation data frame indicates to the controller 2, 2' that the slave device 3, 4 is now in communication mode. In contrast to the sniff mode, the receiver 19 is maintained activated until the preamble signal of a further data frame 300 is detected or until a communication timeout period of e.g. 2 s duration (i.e. longer than the listening period) has elapsed without detection of the preamble signal (step 211). If a preamble signal of a further data frame is detected in step 211, the further data frame is received in step 212. Otherwise, and in case none of the received further data frames are addressed to the slave device, the slave device is switched back to power saving mode (step 214). The same happens if the command contained in the command portion 304 of the further data frame 300 indicates that the communication mode shall be terminated immediately (step 213). However, if the further data frame 300 received in step 212 is not such a termination data frame, the receiver 19 is deactivated in step 214 to go back to step 209 in order to transmit a response. Depending on the command, such response may be a mere confirmation of receipt or may include data requested by the controller 2, 2'. Thus, as long as the controller 2, 2' continues to transmit further data frames 300 to the same slave device 3, 4 such that the preamble signals of the respective further data frames are received before the communication timeout period has elapsed, the slave device 3, 4 stays in communication mode, in which the receiver 19 is only deactivated during the time it takes to transmit a response. In normal operation, the communication mode is terminated by means of a further data frame 300 including in the command portion 304 a termination command.

Upon switching back from communication mode to power saving mode in step 214, the sniff interval is adjusted to be 300 ms in order to reduce the delay time in the case of a further communication attempt by the controller 2, 2'. The same is done in step 216, when a slave device 3, 4 receives a data frame 300 including the communication initiation command in the command portion 304, and determines in step 206 that the address contained in the address portion 303 is not its own address.

In any case, following receipt of a data frame 300 which is either not a communication initiation data frame (step 205) or is a communication initiation data frame addressed to a different device (step 206), the receiver 19 is deactivated for the rest of the sniff interval in step 217. Subsequently, it is determined in step 218 whether the sniff interval is currently 300 ms and whether a predetermined power saving timeout period of e.g. 15 s has elapsed since the sniff interval was last set to 300 ms. Before the end of this timeout period, the sniff interval is left unchanged. If it has elapsed, the sniff interval is changed to its normal value of 3 s in step 219. In this way, as soon as the controller 2, 2' initiates communication with one of its slave devices 3, 4 the delay time is reduced for all of these devices 3, 4, thereby increasing the efficiency of communication in the blood glucose system 1, 1' with its highly non-uniform traffic distribution on the air interface.

With the slave devices 3, 4 operating in this manner, in case communication between the controller 2, 2' and one of the devices 3, 4 is desired, a data frame 300 is prepared in the controller 2, 2' in step 100 (FIG. 3a). Prior to transmitting the data frame 300, the address of the target device is included into the target address portion 303 (step 101), the identifier of the communication initiation command is included into the command portion 304 (step 102), and the number of preamble bytes is chosen such that the preamble period is 325 ms (step 103). Then, the transmitter 9 is activated and deactivated to transmit this data frame 300, and subsequently the receiver 10 is activated for a response period of 100 ms to wait for a response from the target slave device (e.g. confirmation of receipt). It is to be noted that the target slave device 3, 4 will only definitely receive the data frame 300 if its sniff interval is currently 300 ms. In this case, the preamble period chosen in step 103 spans the entire sniff interval. If, however, the sniff interval of the slave device 3, 4 is currently 3 s, the slave device 3, 4 will probably not detect the preamble signal within one of its listening periods and will thus not send a response. Therefore, if it is determined in step 106 that the slave device 3, 4 has not transmitted a response, the number of preamble bytes in the preamble portion 301 of the data frame 300 is increase so as to adjust the preamble period to 3025 ms, i.e. to a value spanning an entire 3 s sniff interval. Then, the data frame 300 is retransmitted (step 108) and the receiver 10 is activated for 100 ms to wait for a response.

After receipt of a response, it is ensured that the respective slave device 3, 4 is in communication mode with its receiver 19 activated. In this situation, a further data frame 300 is prepared (step 110), and in step 111 the address of the slave device 3, 4 is included in the address portion 303, a suitable command is included in the command portion 304 and optionally additional data are included in data portion 305.

The control electronics 12 in combination with the clock 23 always track the time since transmitting the last data frame to the current slave device, and in step 112 the control electronics 12 compare this time with the communication timeout period in order to determine whether the slave device is still in communication mode. If it is determined that the current slave device 3, 4 is still in communication mode, the preamble period is set to 25 ms in step 114. This minimal preamble period is sufficient since the target slave device is in communication mode so that its receiver 19 is activated. However, it is necessary to transmit the further data frames timely enough for the slave device to still be in communication mode, i.e. the time interval between successive data frames must be smaller than the communication timeout period. Otherwise, if the above determination is negative, the controller goes back to step 100 to initiate another communication cycle with the slave device (step 113). Then, the further data frame 300 is transmitted in step 115, followed by activating the receiver 9 for 100 ms to wait for a response (step 116). Thus, the target slave has to respond within 100 ms of receipt of a data frame. If the controller 2, 2' does not receive a response within this response time (step 117), it goes back to step 115 in order to retransmit the further data frame. If it is determined that further commands shall be transmitted to the same slave device (step 118), another further data frame 300 is prepared in step 110. Otherwise, a data frame 300 including a termination command in its command portion 304 is prepared and transmitted to the slave device in step 119 in order to effect its switching back to power saving mode.

In certain cases, a slave device 3, 4, which just has received a further data frame from the controller 2, 2', may not be able to transmit a response within the response time period of the controller 2, 2'. For example, if the further data frame includes a command requesting the slave device 3, 4 to collect data and provide these data to the controller 2, 2', the necessary data may not be available immediately. In such situations, the slave device 3, 4 has the possibility of delaying transmission of the response in step 209 and to perform the steps of FIG. 5a instead. Thus, in step 500 it is determined by means of the control electronics 21 whether the data requested by the controller 2, 2' are currently available. In the affirmative, the method proceeds to step 209 (step 501). Otherwise, a data frame is transmitted that includes a delay time period indication (step 502), and the receiver 18 and the transmitter 19 of the slave device 3, 4 is deactivated for the corresponding delay time period (step 503) in order to save energy. After the delay time period has elapsed (as determined by the control electronics 21 in combination with the clock 24), the receiver 18 is activated in step 504 until a further data frame including a request to transmit the delayed response is received in step 505. Then, the receiver is deactivated in step 506, and the method proceeds to step 209 (step 507) in order to finally transmit the response to the original further data frame.

In order for this delay mechanism to work properly, the controller 2, 2' does not only determine whether a response has been received in step 117, but the control electronics 12 further examine the received response to determine whether it includes a delay time indication (which could e.g. be represented by a suitable command and additional data specifying the delay time period). If no delay time indication is found, the method proceeds to step 118 (step 511). On the other hand, in case a delay time indication is found, the control electronics 12 effect deactivation of the receiver 10 and the transmitter 9 for the corresponding delay time period (step 512) in order to save energy. After the delay time period has elapsed (as determined by the control electronics 12 in combination with the clock 23), the control electronics 12 prepare a further data frame (step 513), include a target device indication (step 514), and include a request command and additional data requesting the target slave device to transmit a response to a particular earlier data frame (step 515). Then, the preamble period is set to 25 ms in step 516 (which is sufficient because the target slave device has activated its receiver after the delay time period has elapsed), and the request data frame is transmitted in step 517. Finally, the method proceeds to step 116 (step 518) to wait for the requested response.

The invention claimed is:

1. A method for wireless transmission of data between components of a blood glucose system including a master controller having a receiver and a transmitter and a slave device having a receiver and a transmitter, the method comprises the steps of:
setting a sniff interval for the slave device to a first sniff interval;
determining whether a preamble data transmission is received within a first interval;
in the event the determining step is true, evaluating whether a remainder of the data frame is a communication initiation data frame and deciding whether an address portion of the data frame includes an address of the slave device;
in the event the evaluating step or the determining step is false, deactivating the receiver of the slave; and
in the event the deciding step is true, deactivating the receiver of the slave device and switching the slave device to a communication mode such that the transmitter of the slave device is activated to transmit a response to the master controller and then the receiver of the slave device is again activated to wait for further data frames from the master controller.

2. The method of claim 1, in which in the communication mode, the method comprises:
transmitting a response from the slave device to the master controller; and
switching the slave device to a power saving mode from the communication mode;
setting a receiver activation frequency to a first frequency upon the switching step and to a second frequency smaller than the first frequency if no communication data frame is received during a predetermined power saving timeout period.

3. The method of claim 2, in which the communication initiation data frame is transmitted in which the preamble period for transmission of the data frame exceeds the length of the cycle duration corresponding to the first frequency value.

4. The method of claim 3, in which no response is received by the master controller during a response period, retransmitting the communication initiation data frame in which the preamble period is increased and exceeds the length of the cycle duration corresponding to the second frequency value.

5. The method according to claim 4, further comprising at least another slave device including a blood glucose meter, in which the at least another slave device performs the same steps as the slave device in the form of an infusion pump.

6. The method according to claim 5, further comprising
transmitting an indication of a target slave device in the communication initiation data frames by the controller in order to address each communication initiation data frame to a particular slave device, and
in case the particular slave device receives the preamble signal corresponding to a communication initiation data frame during a listening period then:
a) maintaining the receiver of the slave device active at least until the target device indication has been received, and
b) maintaining the receiver of the slave device active until the remainder of the communication initiation data frame has been received if the slave device is the target slave device,
or, in case the slave device is not the target slave device then:
maintaining the slave device in the power saving mode and
setting the activation frequency for the slave device to a third frequency value greater than the second frequency value and subsequently setting the activation frequency to the second frequency value if no communication initiation data frame is received for a predetermined timeout period.

7. The method according to claim 1, in which the third frequency value is identical to the first frequency value.

8. The method according to claim 1, in which the controller only transmits communication initiation data frames.

9. The method according to claim 8, further comprising the following steps:
following transmission of a communication initiation data frame, activating the transmitter of the controller for at least one further transmission period to transmit at least one further data frame including a preamble portion which is chosen such that the preamble signal is transmitted for a preamble period, and
following transmission of each of the at least one further data frame, activating the receiver of the controller for a response period, in which all data frames transmitted by the controller include a command portion in which a command is included, including a communication initiation command in the command portion of any communication initiation data frame to indicate that this data frame is a communication initiation data frame, or
in case a slave device receives the preamble signal during a listening period while it is in the power saving mode: a) maintaining the receiver of the slave device active at least until the command included in the command portion of the data frame has been received, and b) maintaining the slave device in the power saving mode in case the command is not the communication initiation command, and
in case a slave device receives the preamble signal while it is in the communication mode:
a) maintaining the receiver of the slave device active at least until the command included in the command portion of the data frame has been received, and
b) if the command is not the communication initiation command and the slave device is the intended recipient of the data frame, maintaining the receiver of the slave device active until the remainder of the data frame has been received, and
activating and deactivating the transmitter of the slave device to transmit a response to the controller.

10. The method according to claim 8, in which the communication mode is terminated if no data frame for the respective slave device is received for a predetermined communication timeout period, and in which in communication mode the receiver of the respective slave device is maintained active whenever its transmitter is not activated to transmit a response.

11. The method according to claim 10, further comprising the steps of
- tracking at the controller the time since transmitting the last data frame to a particular slave device,
- determining at the controller, prior to transmitting a data frame to the same slave device, based on a comparison between the tracked time and the predetermined communication timeout period whether this slave device is expected to still be in communication mode, and,
- if it is determined that the slave device is expected to still be in communication mode, initially transmitting the data frame such that the preamble period spans a time period shorter than the cycle durations corresponding to the first frequency value and the second frequency value.

12. The method according to claim 11, further comprising the steps of:
- including a delay time period indication into a response transmitted by a slave device to a particular first data frame to indicate that the actual response will be transmitted later,
- deactivating the transmitter and the receiver of both the slave device and the controller for the indicated delay time period, activating the transmitter of the controller after the end of the delay time period to transmit a second data frame requesting the response to the first data frame,
- activating the receiver of the slave device after the end of the delay time period to wait for the receipt of the second data frame, and
- subsequently activating the transmitter of the slave device to transmit the requested response to the controller.

13. The method according to claim 10, in which a data frame including a termination command is transmitted by means of the controller to a slave device in communication mode, and in which the communication mode of the slave device is terminated upon receipt of this data frame.

14. The method according to claim 10, in which the transmission of at least one communication initiation data frame by the controller is initiated by user request.

15. The method according to claim 10, further comprising the steps of periodically generating a timer event in the controller, and transmitting a communication initiation data frame by the controller upon each occurrence of a timer event.

16. The method according to claim 15, further comprising the steps of:
- choosing the frequency at which the timer events occur to have the second frequency value such that the second frequency value comprises an integral multiple of the timer event frequency, including a time reference in each communication initiation data frame initiated by a timer event,
- examining the time reference upon receipt at a slave device, and synchronizing by the time reference the start times of the listening periods with the timer events.

17. The method according to claim 1, in which the slave device comprises at least one of an infusion pump and blood glucose meter and in which the master controller comprises at least one of an infusion pump and a blood glucose meter.

* * * * *